(12) United States Patent
Nistico et al.

(10) Patent No.: US 9,033,502 B2
(45) Date of Patent: May 19, 2015

(54) OPTICAL MEASURING DEVICE AND METHOD FOR CAPTURING AT LEAST ONE PARAMETER OF AT LEAST ONE EYE WHEREIN AN ILLUMINATION CHARACTERISTIC IS ADJUSTABLE

(75) Inventors: Walter Nistico, Berlin (DE); Jan Hoffmann, Berlin (DE); Eberhard Schmidt, Kleinmachnow (DE)

(73) Assignee: SENSOMOTORIC INSTRUMENTS GESELLSCHAFT FUR INNOVATIVE SENSORIK MBH, Teltow (DE)

( * ) Notice: Subject to any disclaimer, the term of this patent is extended or adjusted under 35 U.S.C. 154(b) by 0 days.

(21) Appl. No.: 14/005,307

(22) PCT Filed: Mar. 15, 2012

(86) PCT No.: PCT/EP2012/054609
§ 371 (c)(1),
(2), (4) Date: Nov. 14, 2013

(87) PCT Pub. No.: WO2012/126810
PCT Pub. Date: Sep. 27, 2012

(65) Prior Publication Data
US 2014/0055747 A1    Feb. 27, 2014

(30) Foreign Application Priority Data

Mar. 18, 2011    (EP) ..................... 11158891
Jul. 13, 2011    (EP) ..................... 11173753

(51) Int. Cl.
A61B 3/14    (2006.01)
A61B 3/113    (2006.01)

(52) U.S. Cl.
CPC .. *A61B 3/14* (2013.01); *A61B 3/113* (2013.01)

(58) Field of Classification Search
CPC ...... A61B 3/12; A61B 3/1208; A61B 3/1216; A61B 3/1225; A61B 3/1233; A61B 3/1241; A61B 3/14; A61B 3/15; A61B 3/152; A61B 3/18
USPC ......................... 351/205–210, 213
See application file for complete search history.

(56) References Cited

U.S. PATENT DOCUMENTS

| 4,145,122 A | 3/1979 | Rinard et al. |
| 5,092,669 A | 3/1992 | Anderson |
| 6,163,281 A | 12/2000 | Torch |
| RE39,539 E | 4/2007 | Torch |

(Continued)

FOREIGN PATENT DOCUMENTS

| WO | 2004/066097 A2 | 8/2004 |
| WO | 2005/094667 A2 | 10/2005 |
| WO | 2010/083853 A1 | 7/2010 |

*Primary Examiner* — Suchin Parihar
*Assistant Examiner* — William R Alexander
(74) *Attorney, Agent, or Firm* — Sughrue Mion, PLLC

(57) ABSTRACT

The invention relates to an optical measuring device (1) for capturing at least one parameter of at least one eye (10*l*, 10*r*) of a test person (31) wearing the optical measuring device (1), comprising a frame (4), which is configured to fix the optical measuring device (1) to the head of the test person (31), at least one capturing unit (3*l*, 3*r*), which is configured to optically capture the at least one parameter of the at least one eye (10*l*, 10*r*), and an illumination unit (9, 21, 22) for illuminating the at least one eye (10*l*, 10*r*), wherein an illumination characteristic is adjustable by means of the illumination unit (9, 21, 22).

22 Claims, 10 Drawing Sheets

(56) References Cited

U.S. PATENT DOCUMENTS

Figure 1A:
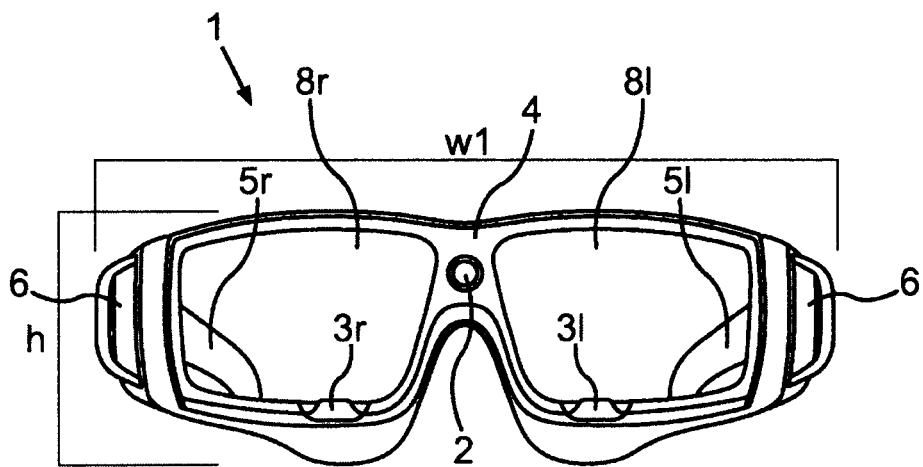

| | | |
|---|---|---|
| 2002/0036750 A1* | 3/2002 | Eberl et al. .................... 351/207 |
| 2004/0196433 A1 | 10/2004 | Durnell |
| 2010/0188638 A1* | 7/2010 | Eberl et al. .................... 351/221 |
| 2010/0220291 A1 | 9/2010 | Horning et al. |
| 2011/0077548 A1 | 3/2011 | Torch |

\* cited by examiner

Measure
0,5m

OPTICAL MEASURING DEVICE AND METHOD FOR CAPTURING AT LEAST ONE PARAMETER OF AT LEAST ONE EYE WHEREIN AN ILLUMINATION CHARACTERISTIC IS ADJUSTABLE

The invention relates to an optical measuring device for capturing at least one parameter of at least one eye of a test person wearing the optical measuring device, comprising a frame, which is configured to fix the optical measuring device to the head of the test person, at least one capturing unit, which is configured to optically capture the at least one parameter of the at least one eye, and an illumination unit for illuminating the at least one eye. The invention also relates to a method for capturing at least one parameter of at least one eye.

It is known from the prior art to use head mounted eye tracker devices. U.S. RE39,539 E discloses an apparatus for monitoring movement of a person's eye. The system includes a frame that is worn on a person's head, an array of emitters on the frame for directing light towards the person's eye, and an array of sensors on the frame for detecting light from the array of emitters. The sensors detect light that is reflected off of respective portions of the eye or its eyelid, thereby producing output signals indicating when the reflective portion of the eye is covered by the eyelid. The system allows to monitor the persons level of drowsiness.

U.S. Pat. No. 6,163,281 discloses a system and method for communication using movement of a person's eye, including an emitter for directing light towards an eye, a sensor for detecting emitted light from the emitter, and a processor coupled to the sensor for converting sequential light intensity signals received from the sensor to a stream of data, and/or for converting the signals into an understandable message. US 2004/0196433 A1 discloses an eye tracking system for monitoring the movement of a user's eye comprising an eye camera and a scene camera for supplying to interlace electronics video data indicative of an image of the user's eye and an image of the scene observed by the user. In addition, the system incorporates a frame grabber for digitizing the video data and for separating the eye and scene data into two processing channels, and a spot location module for determining from the video data the location of a reference spot formed on the user's eye by illumination of the user's eye by a point source of light. The system further incorporates a pupil location module in order to determine the user's line of gaze.

WO 2010/83853 A1 discloses a gaze point detection system with one or more infrared signal sources to be placed in a test scene as reference points, at least one pair of eye glasses worn by a test subject, and a data processing and storage unit for calculating a gaze point of the person. The eye glasses comprise an image sensor adapted to detect IR signals from the at least one IR signal source and to generate an IR signal source tracking signal, an eye tracking unit adapted to determine the gaze direction of the test subject person and to generate an eye tracking signal, and a camera unit adapted to acquire a test scene picture.

WO 2004/066097 A2 discloses an eye tracking system for displaying a video screen pointer at a point of regard of a users gaze. The system comprises a camera focused on the user's eye, a support connected to the camera for fixing the relative position of the camera to the user's pupil, and a computer having a CPU and an eye tracking interface. By determining the center of the eye, a pointer on the video display screen can be displayed at the point of regard. WO 2004/066097 A2 discloses an optical measuring device according to the preamble of the present application.

US 2010/0220291 A1 discloses an eye tracking system with a transparent lens, at least one light source, and a plurality of light detectors. The transparent lens is adapted for disposal adjacent an eye. At least one light source is disposed within the transparent lens and is configured to emit light towards the eye. The at least one light source is transparent to visible light. The plurality of light detectors is disposed within the transparent lens and is configured to receive light that is emitted from the at least one light source and is reflected off of the eye. Each of the light detectors is transparent to visible light and is configured, upon receipt of light that is reflected off of the eye, to supply an output signal.

Known head mounted eye trackers suffer from the disadvantage that environmental stray light being reflected on the test person's eye may negatively influence the eye tracking functionality. Cameras monitoring the test person's eyes may not be able to distinguish between features of the eyes explicitly used for keeping track of the eye movement and features, such as reflections, arising from environmental lighting conditions. In general, the illumination situation is not very well defined. Reliable eye tracking is often compromised by environmental conditions and undesired stray light disturbing the tracking mechanism. Thus, known head mounted eye tracker devices usually suffer from a limited accuracy and robustness. To improve detection accuracy, time consuming and difficult calibration procedures are required. Furthermore, existing eye tracking devices need extensive multi-point calibration routines in order to correct for various individual characteristics of the eye(s) of the user. One such characteristic is the individual corneal astigmatism or non-sphericity of the cornea—which for approximately a third of the population is so significant that it needs optical correction and that is also so significant that it needs individual correction through calibration for an eye tracker.

An objective of the present invention is to provide an optical measuring device and a method which allow for a more reliable capturing of at least one parameter characterizing an eye.

This task according to the invention is solved by an optical measuring device having the features according to patent claim 1, and a method having the features according to patent claim 9. Advantageous embodiments of the invention are the subject matter of the independent claims and the description.

The optical measuring device according to the invention serves for capturing at least one parameter of at least one eye of a test person wearing the optical measuring device. The optical measuring device comprises a frame, which is configured to fix the optical measuring device to the head of the test person, at least one capturing unit, which is configured to optically capture the at least one parameter of the at least one eye, and an illumination unit for illuminating the at least one eye. According to the invention an illumination characteristic is adjustable by means of the illumination unit.

This way, a very well defined illumination situation can be created. With the illumination unit reflections on the test person's eyes can be deliberately created, which may then be captured by the capturing unit. By correlating the capturing performed by the capturing unit with the illumination characteristic according to a lock-in similar technique (periodic subtraction of a background signal from a measurement signal) background and stray light can be very well suppressed. The capturing unit may thus become insensitive to environmental stray light. Detection accuracy and eye tracking capability is very high. The illumination characteristic can serve as a recognition pattern for the capturing unit. Complicated calibration procedures are not necessary.

With the optical measuring device it is possible to directly assess the corneal astigmatism by means of a structured illumination. This is usually done with separate medical diagnostic devices (keratometers). According to an embodiment of the present invention this measurement capability is advantageously integrated into a headmounted device and combined with an eye tracker, thereby integrating the assessment and correction of corneal astigmatism for the structured illumination instead from multiple calibration points.

Advantageously, the illumination unit is configured to be adjustable with regard to a temporal illumination sequence and/or a spatial illumination distribution. The illumination unit may comprise a single illumination element. Then, the temporal illumination sequence can be achieved by varying the temporal light emission characteristics of the illumination element. The temporal illumination sequence may then be given by an on/off switching frequency. The illumination unit may alternatively comprise two or more illumination elements. A temporal illumination sequence can then be given by correlated or anti-correlated switching of the individual illumination elements. For each illumination element within the illumination unit a different temporal illumination or light emission pattern can be realized. The temporal frequency of emitted light intensity of each individual illumination element may depend on the respective illumination characteristic of some or all other illumination elements. The spatial illumination distribution can be achieved by correlated illumination time traces of individual illumination elements. Consequently, a very well defined illumination pattern can be created, which establishes a very well defined illumination environment for the at least one eye. The more artificial the illumination pattern is, the easier it is to distinguish it from environmental stray light. Furthermore the illumination pattern can be created such that for two different sensor types, e.g. a camera sensor and a photo diode (array) different illuminations specifically suited to the sensitivity and resolution characteristic of the respective sensor type are shone on the eye(s).

Advantageously, the illumination unit is attached to the frame in such a way that with the optical measuring device fixed to the head of the test person it faces the at least one eye, and is configured to emit radiation in such a way that the radiation at least partly hits the at least one eye. This way, reflections in the eyes can be created deliberately. The reflections then also show the same illumination pattern as the illumination unit. The reflections can be easily captured by the capturing unit and the illumination pattern can serve as a distinguishing feature to discriminate between deliberate reflections and reflections resulting from undesired stray light. The detection accuracy is highly improved.

Advantageously, the illumination unit comprises at least two illumination segments which, with regard to their luminosity and/or luminous color and/or main radiation direction and/or temporal sequence of the light emission, are separately adjustable. The illumination segments may be identical to the illumination elements of the illumination unit. An illumination segment may be a separate, individual and with regard to its illumination characteristics homogenous entity within the illumination unit. Different illumination segments may then be spatially separated or easily distinguishable with respect to their illumination characteristics. Luminosity, luminous color, main direction of radiation and temporal illumination sequence are characteristics that can be easily captured and discerned by the capturing unit.

In one embodiment the illumination unit may comprise at least one optical wave guide and/or at least two illuminants, in particular light emitting diodes. Light emitting diodes are long lived, do not require much power and have very well defined light emission characteristics. Consequently, they are very well suited for a mobile optical measuring device. With optical wave guides and light emitting diodes point source like illumination can be realized. Spatial illumination patterns may thus be very well defined.

Advantageously, the illumination unit may be configured to emit visible light. Additionally or alternatively the illumination unit may be configured to emit light in the infrared spectral range, particularly in the wavelength range between 750 nanometers and 1000 nanometers. Infrared light can be distinguished very easily from unwanted environmental stray light. This way, detection accuracy is further improved.

Advantageously, the frame comprises at least one frame element for receiving an eyeglass lens, wherein with the optical measuring device fixed to the head of the test person the portion framed by the frame element is positioned in front of the at least one eye of the test person, and the illumination unit is arranged on or within the frame element. Consequently, no additional elements for holding the illumination unit are required. In particular, the optical measuring device can be designed as spectacle device which can be worn as conventional eye-glasses by the test person. The illumination unit would then be fully integrated into the frame and the overall device would resemble a usual eye-glass device. This increases acceptance by the test person. In particular, the illumination unit may then comprise several individual illumination segments or illumination elements which may be positioned in a circular manner in a 360° circumference around each eye-glass lens. A very well defined spatial illumination distribution can be realized.

Advantageously, the at least one captured parameter concerns an orientation and/or a position and/or an eyelid closure and/or a pupil diameter and/or limbus characteristic and/or a sclera characteristic and/or an iris characteristic and/or a characteristic of a blood vessel and/or a cornea characteristic of the at least one eye. In particular the at least one captured parameter may concern a cornea radius (anterior, posterior), an eyeball radius, a distance pupil-center to cornea-center, a distance cornea-center to eyeball-center, a distance pupil-center to limbus center, a cornea keratometric index of refraction, a cornea index of refraction, a vitreous humor index of refraction, a distance crystalline lens to eyeball-center and to cornea center and to corneal apex, a crystalline lens index of refraction, a visual axis orientation, an optical axis orientation, a pupil axis (achromatic axis) orientation, a line of sight orientation, an astigmatism degree (diopters) and orientation angle of flat and steep axis, an iris diameter, pupil diameters (pupil major and minor axes), pupil area), limbus major and minor axes, eye cyclo-torsion, eye intra-ocular distance, eye vergence, statistics over eye adduction/abduction and statistics over eye elevation/depression. The optical measuring device can then work as an eye tracking device.

The method according to the invention serves for capturing at least one parameter of at least one eye of a test person and comprises the following steps:
  fixing an optical measuring device to the head of a test person, the optical measuring device comprising at least one capturing unit and one illumination unit;
  illuminating the at least one eye by means of the illumination unit;
  optically capturing the at least one parameter of the at least one eye by means of the capturing unit;
  setting an illumination characteristic; and
  illuminating the at least one eye by means of the illumination unit according to the set illumination characteristic.

Advantageously, in the step of illuminating the at least one eye the illumination unit is regulated in dependency of a temporal illumination sequence and/or a spatial illumination distribution and/or an illumination pattern.

Advantageously, the step of optically capturing the at least one parameter of the at least one eye comprises the following sub-steps:

optically capturing of at least two light reflections and/or features of the at least one eye; and determining the at least one parameter of the at least one eye by means of the captured light reflections and/or features.

In particular, the at least two light reflections can be deliberately generated by the illumination unit. In one embodiment a first light reflection of the at least two light reflections may be generated by a first illumination element of the illumination unit while a second light reflection of the at least two light reflections may be generated by a second illumination element of the illumination unit. The at least two light reflections may then directly reflect an illumination pattern realized by the illumination unit. Alternatively, the illumination unit may solely be used for illuminating the eye such that the features of the at least one eye become detectable by the respective capturing unit. For this, a specific illumination color could be used.

Advantageously, the at least two light reflections and/or features are then captured at different illuminations caused by the illumination unit.

In one embodiment, the method comprises the following additional steps:

capturing data which concern a viewing behavior of the test person and/or an eye motion characteristic and/or a pupil change and/or an environmental condition and/or inputs of the test person;

in dependency on the captured data setting an illumination program for the temporal and/or spatial illumination distribution and/or the illumination pattern; and regulating the temporal illumination sequence and/or the spatial illumination distribution and/or the illumination pattern according to the said illumination program.

This way the illumination program can be dynamically adjusted to the respective viewing situation. For different viewing behaviors of the test person, eye motion characteristics, pupil diameters or environmental lighting conditions different illumination programs may be suited best. The capturing unit may determine such a change and based on this information the illumination program may be adjusted automatically. If the test person recognizes that the detection accuracy needs improvement it may also alternatively or additionally be able to set the illumination program manually. If the optical measuring device is used in darkness (for example during the night), a different illumination program may lead to better detection results than an illumination program used during daylight conditions. The method for capturing the at least one parameter may be adjusted automatically to this environmental change and thus allow for very good eye tracking results even under highly changing environmental conditions.

Further features of the invention derive from the claims, the figures, and the description of the figures. All features and feature combinations previously mentioned in the description as well as the features and feature combinations mentioned further along in the description of the figures and/or shown solely in the figures are not only usable in the combination indicated in each case, but also in different combinations or on their own.

Figure 1B:
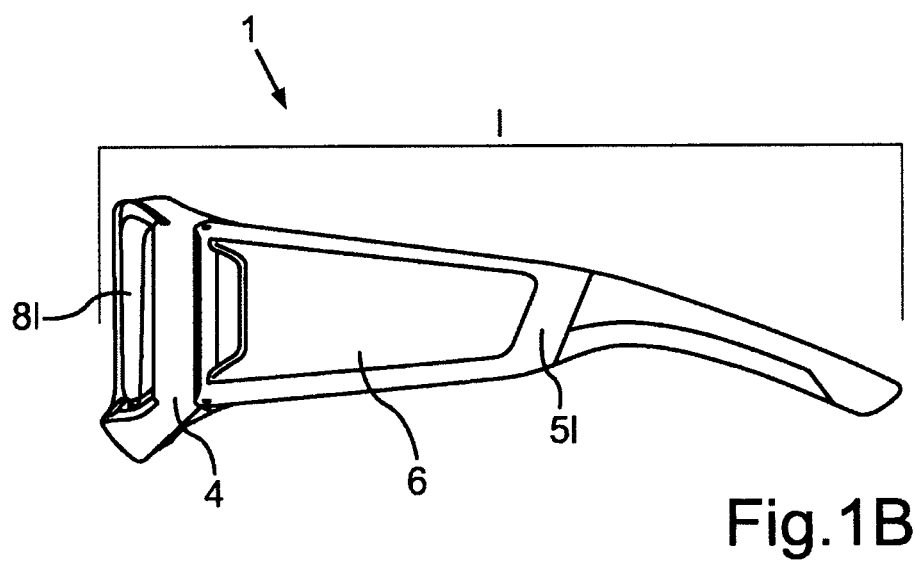
Figure 1C:
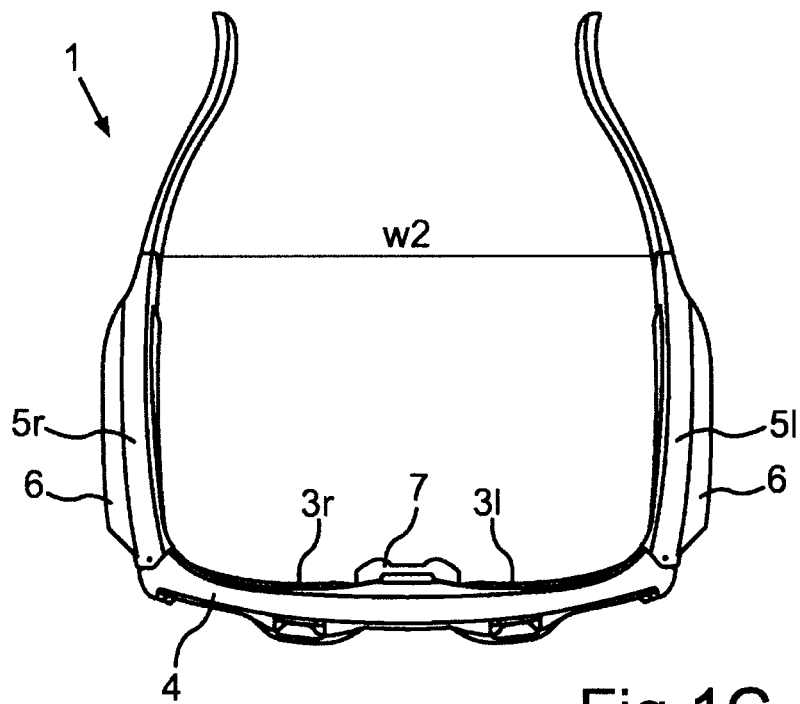
Figure 1D:
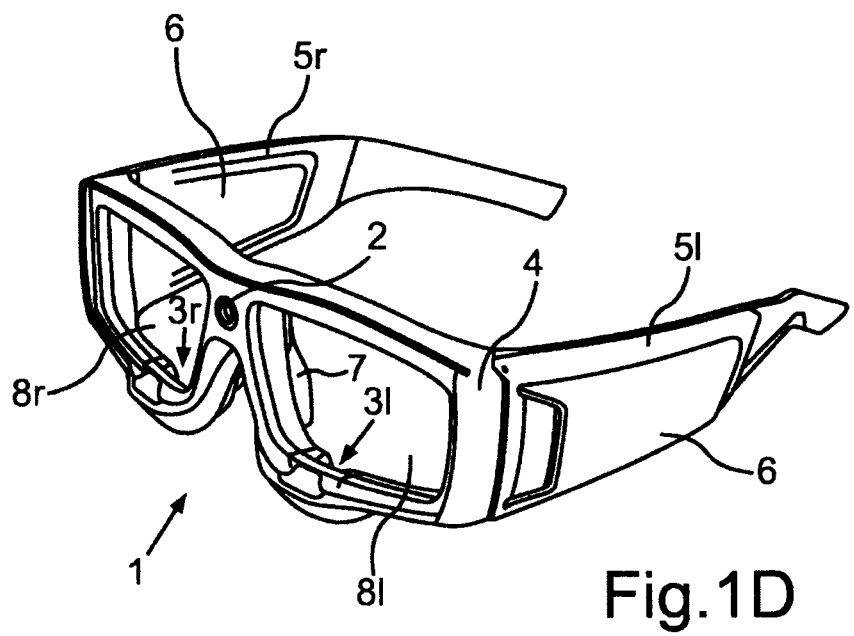
Figure 2:
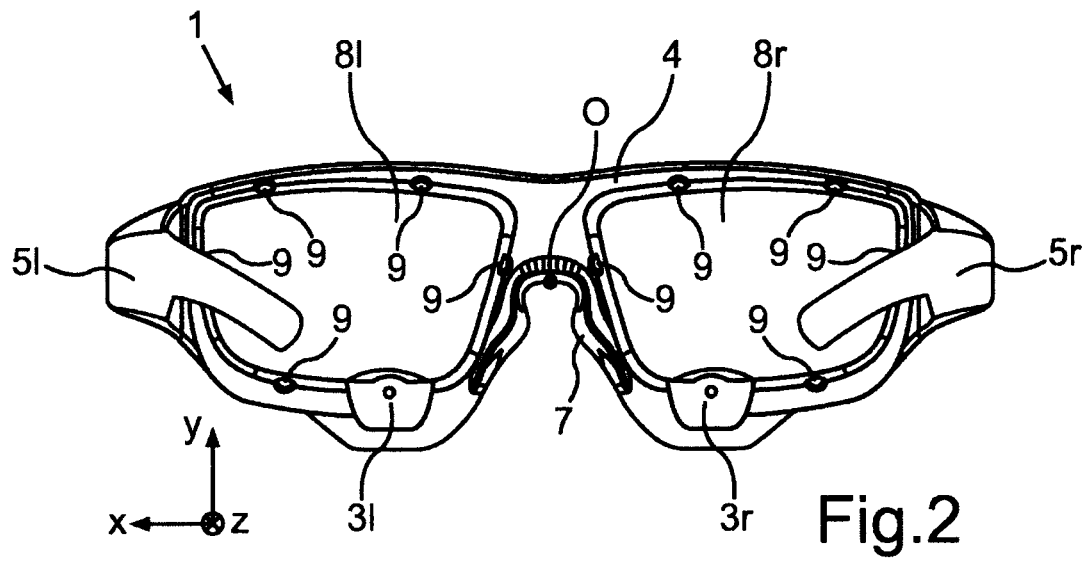
Figure 3:
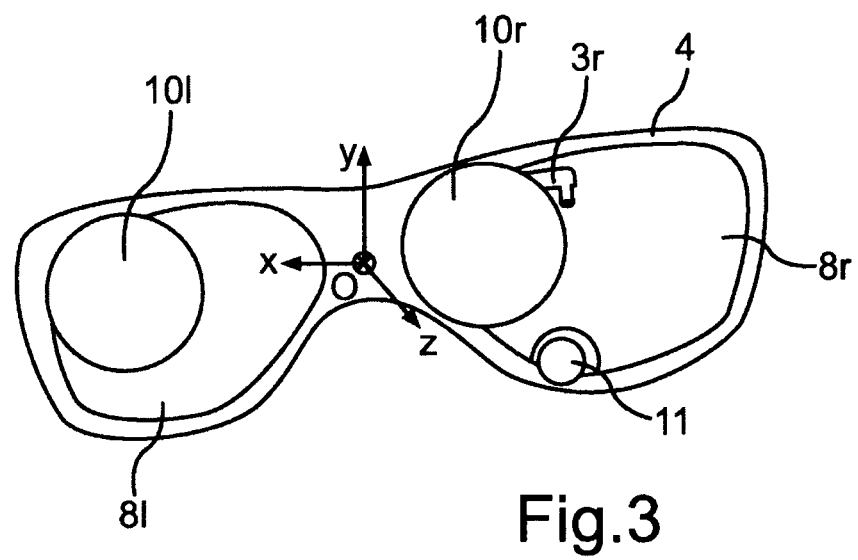
Figure 4:
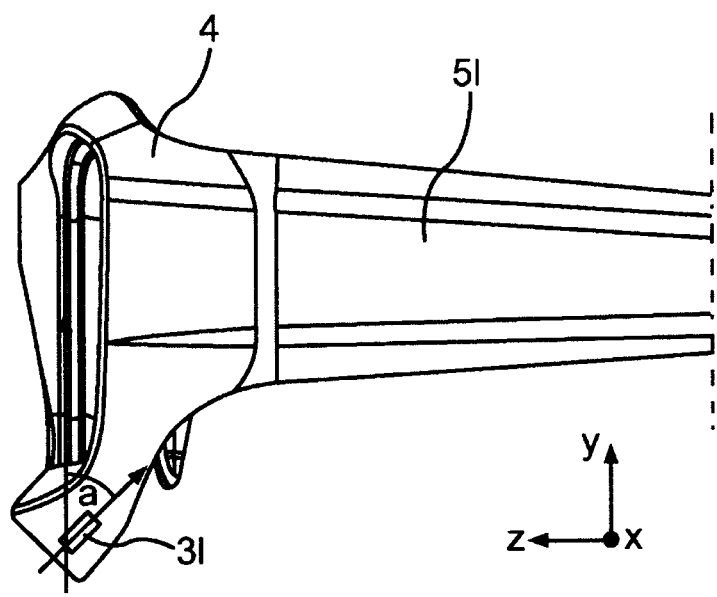
Figure 5:
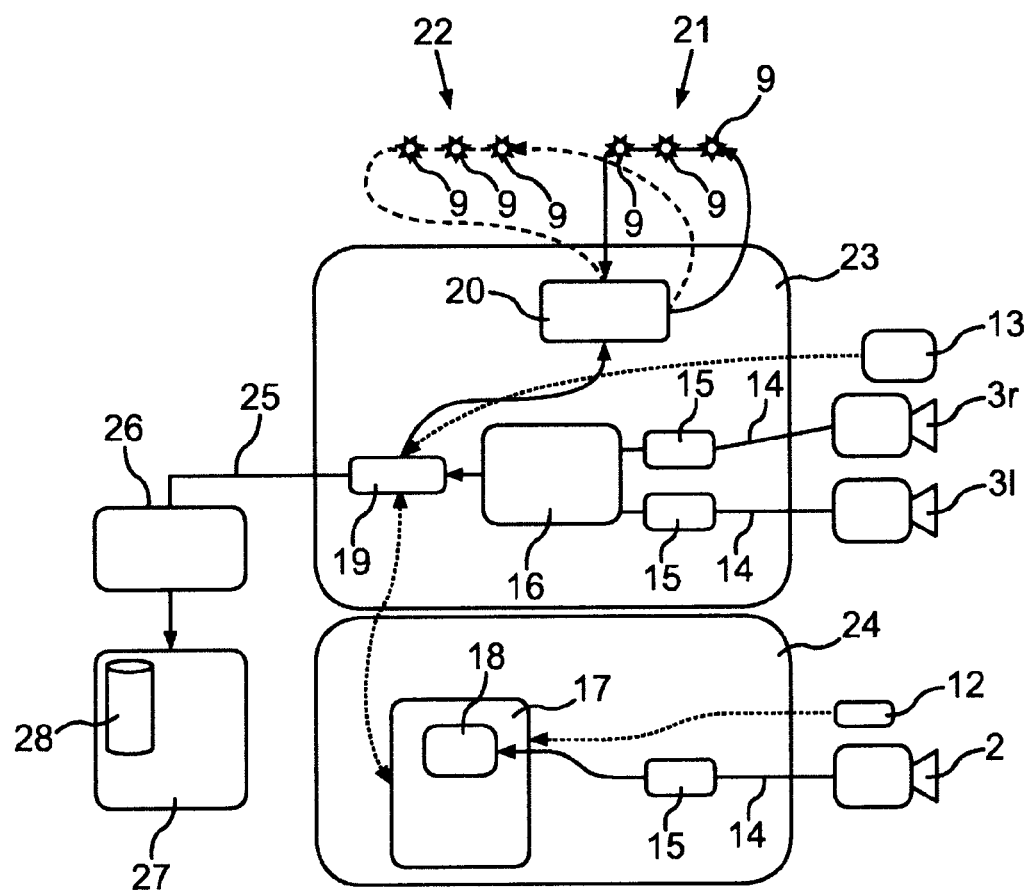
Figure 6A:
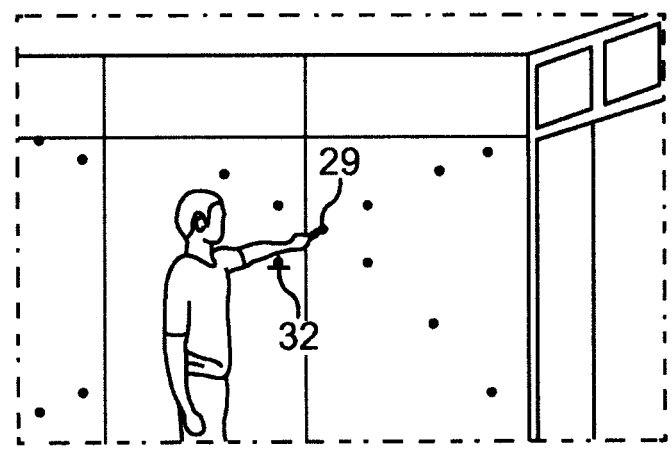
Figure 6B:
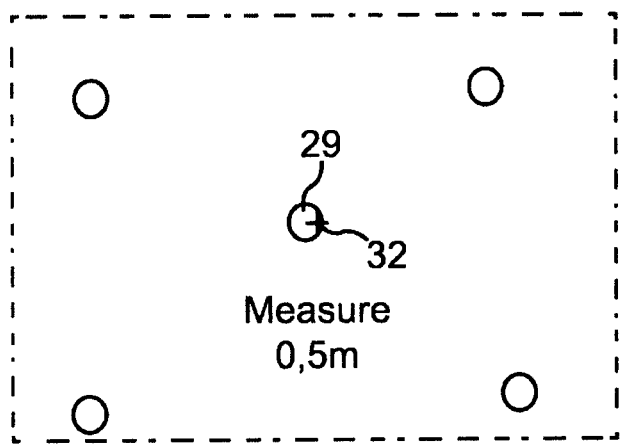
Figure 7:
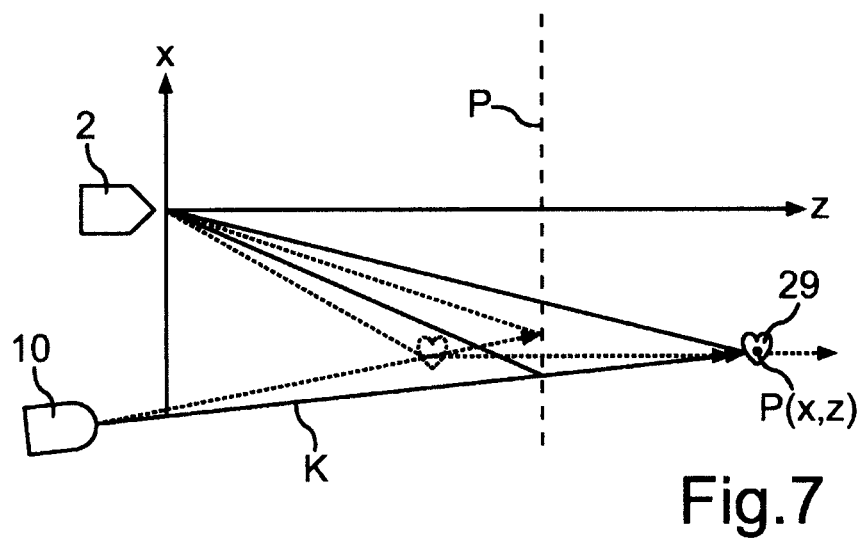
Figure 8:
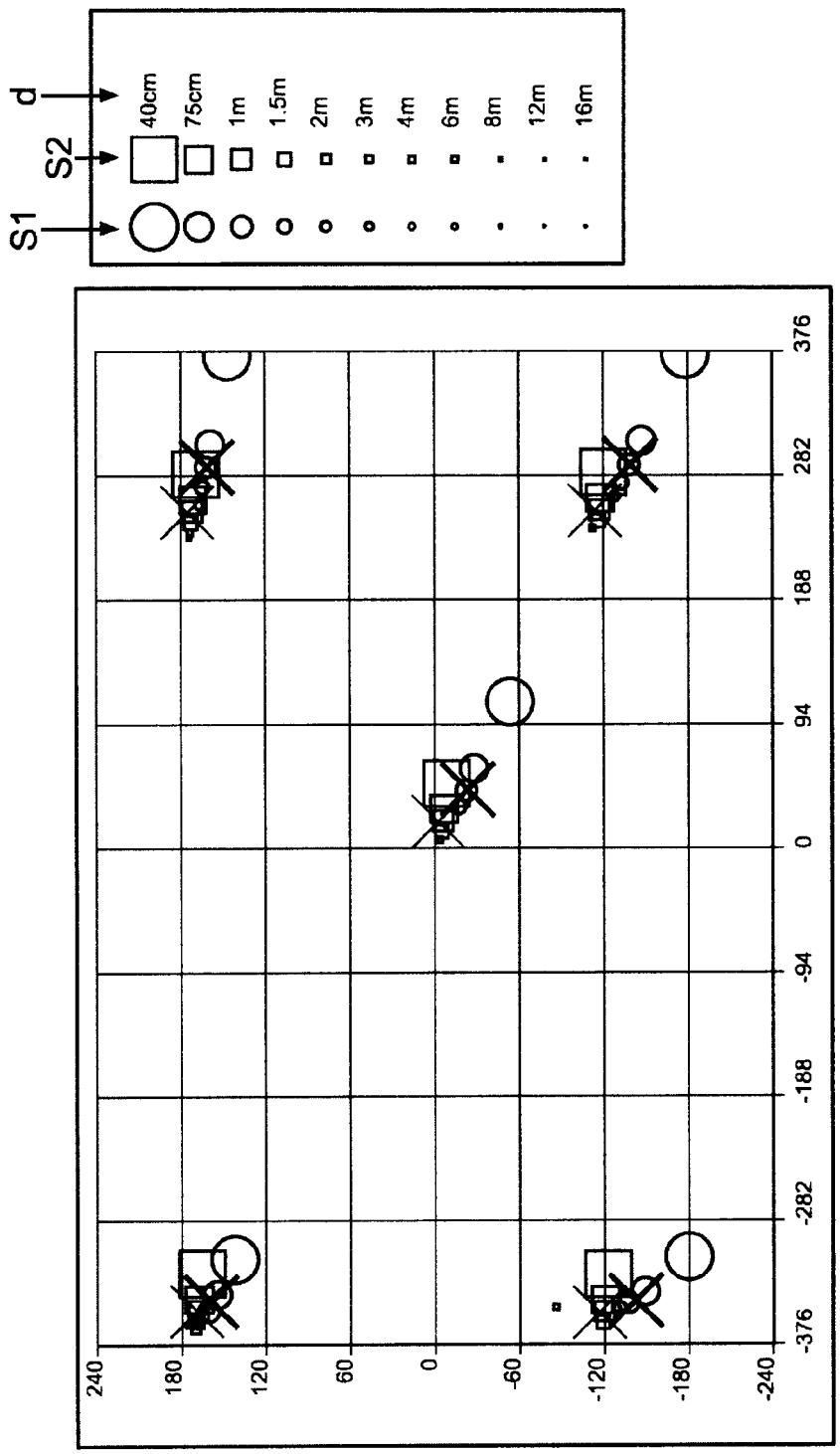
Figure 9A:
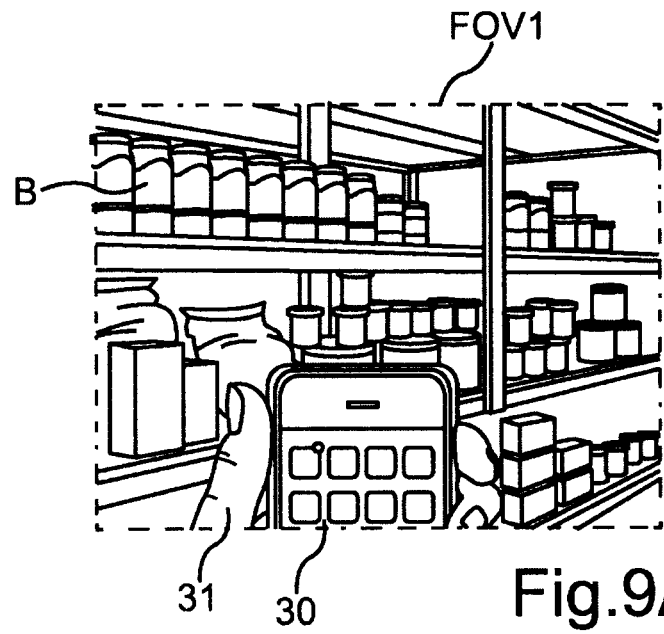
Figure 9B:
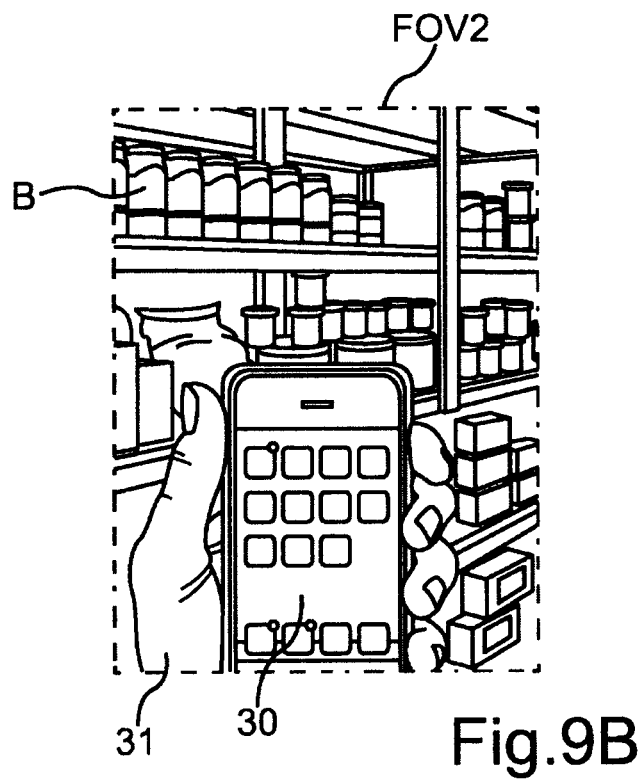
Figure 10A:
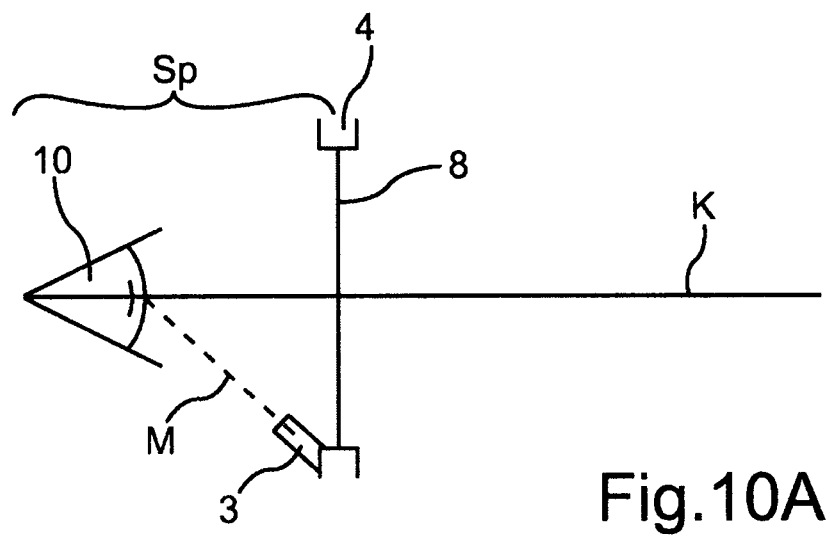
Figure 10B:
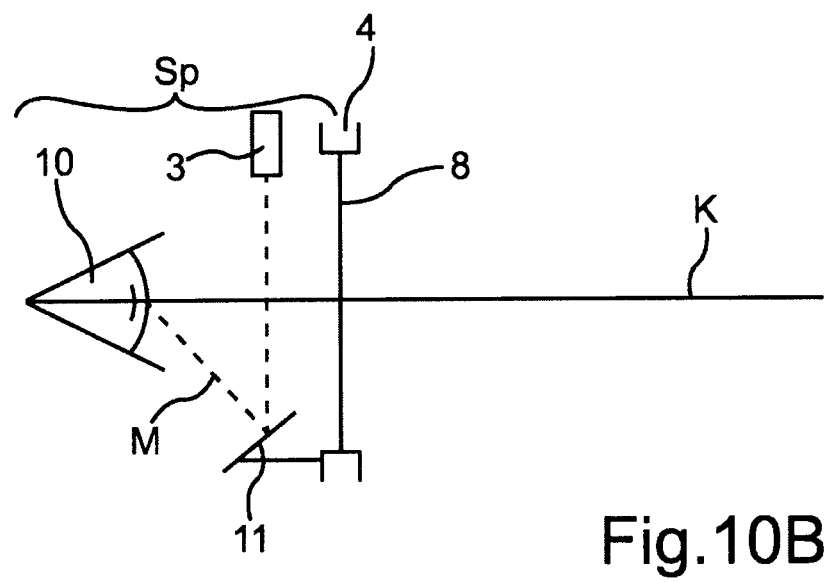

The invention is now explained in more detail with reference to individual preferred embodiments and with reference to the attached drawings. These show in:

FIG. 1A a front view of a spectacle device according to an embodiment of the invention;

FIG. 1B a side view of the spectacle device of FIG. 1A;

FIG. 1C a top view of the spectacle device of FIG. 1A;

FIG. 1D a perspective view of the spectacle device of FIG. 1A;

FIG. 2 a rear view of a spectacle device;

FIG. 3 a schematic rear view of a spectacle device with an eye camera making use of a deflection element to direct its optical path onto the eye;

FIG. 4 a side view of a spectacle device schematically showing the orientation of an eye camera;

FIG. 5 a schematic view of individual electronic components comprised by a spectacle device;

FIG. 6A a picture with a symbol indicating a large parallax error attained with an optical measuring device according to the prior art;

FIG. 6B a picture showing a symbol indicating the lack of a parallax error with a spectacle device according to an embodiment of the invention;

FIG. 7 a parallax error model;

FIG. 8 a diagram comparing parallax errors of measuring devices according to the prior art and according to an embodiment of the invention;

FIG. 9A a first field of view acquired by a scene camera;

FIG. 9B a second field of view acquired by the scene camera;

FIG. 10A a schematic side view of a spectacle device were the optical path of an eye camera extends in a straight line from the eye camera to an eye; and FIG. 10B a schematic side view of a spectacle device where the optical path of an eye camera extends from the eye camera via a mirror to the eye.

In the figures same elements or elements of the same function are equipped with the same reference signs. FIGS. 2, 3, and 4 show the same reference frame with a Cartesian coordinate system and perpendicular axes x, y and z.

FIGS. 1A to 1D show an optical measuring device which has the form of a spectacle device 1 or eye tracking device, respectively. The spectacle device 1 is designed such that a person can wear it on its head just like a normal pair of glasses. It comprises a frame 4 with two side bars 5l and 5r which support the spectacle device 1 on the ears of the person who is wearing it. Furthermore, the spectacle device 1 is held in place on the head by a nose support 7. The mainframe has a specific width w1 and height h. Its length 1 depends on the length of the sidebars 5l and 5r. As can be seen in FIG. 1C the sidebars 5l and 5r are hinged to the front part of the frame 4 such that the distance w2 between the side bars 5l and 5r can be enlarged or reduced (see dashed sidebar configuration for sidebar 5l in FIG. 1C).

Alternatively, the optical measuring device may not be designed in form of a regular pair of eye glasses, but may be designed such that it resembles a helmet, forming a frame, with a face shield, forming a frame insert.

Above the nose support 7 in the frame 4 a scene camera 2 is installed. It can either be attached to or integrated into the frame 4. With the scene camera 2 virtually a similar field of view can be captured as seen by a test person when wearing the spectacle device 1. In the lower part of the frame 4 the spectacle device 1 contains two eye cameras 3l and 3r. When the spectacle device 1 is worn by a person the person's eyes can be captured by the eye cameras 3l and 3r, which are integrated into the frame 4 at a suitable angle. Eye cameras 3l and 3r are designed to observe the person's left eye and right eye, respectively, i.e. capture characteristics of the person's eyes.

The frame 4 contains two openings which are filled with eye glass lenses 8l and 8r thus forming frame inserts. The pictures acquired by the scene camera 2 and the eye cameras 3l and 3r lead to signals which are processed in one or several pre-processing units 6 integrated into the sidebars 5l and 5r.

FIG. 2 shows an inside view of the spectacle device 1. Along the rim of the frame part enclosing the eye glass lenses 8l and 8r several Light Emitting Diods (LEDs) 9 are located in a ring arrangement. When the spectacle device 1 is worn by a person, those LEDs 9 can illuminate the eyes of the test person in a defined way. The LEDs 9 will cause reflections on the eyes of the test person (cornea reflections) for all possible gaze angles. Those reflections can be detected by the eye cameras 3l and 3r and can be used for eye tracking.

The LEDs 9 can be switched on an off individually, in groups or all together following a specific time pattern, strobe characteristic or spatial variation. The on-off-switching-frequency of different LEDs 9 or groups of LEDs 9 may vary. Certain groups of LEDs 9 may get switched on exactly when other groups of LEDs 9 get switched off. A specific spatial and temporal correlation pattern may be implemented with regard to the switching and thus illumination characteristics. This way a reflection pattern can be created on the eyes that can be recognized easily by the eye cameras 3.

The overall setup with the most important electronic components is shown in FIG. 5. The eye cameras 3l and 3r are connected to specific camera electronics 15 by 100 mm long cables 14. In particular, the cameras 3l and 3r comprise only basic electronic components while their major electronic components are located within the camera electronics 15. This way, the primarily "optical part" of the cameras 3l and 3r can be located remote to the primarily "electronic part" within the camera electronics 15. Both parts can then be connected by flex-PCB cables 14. This way, the optical sensor and the basic electronic components within the cameras 3l and 3r form a very small and highly compact entity while bulkier electronic components within the electronics 15 can be placed on more spacious integrated circuit boards elsewhere. The electronics 15 are connected to a pre-processing unit 16 which can process the signals from the eye cameras 3l and 3r. The pre-processing unit 16 can be identical to the pre-processing unit 6 located in the sidebars 5l and 5r of the spectacle device 1. The pre-processing unit 16 is connected to a USB-hub 19. The LEDs 9 installed in the frame 4 form a first and a second IR LED chain 21 and 22 arranged in a ring configuration around the eye glass lenses 8l and 8r. The IR LED chains 21 and 22 are connected to an IR LED constant current source 20, which is also connected to the USB-hub 19. The USB-hub 19 additionally serves as a power source for the IR LED constant current source 20. The LEDs 9 of the IR LED chains 21 and 22 can be switched on an off individually. To achieve this, they may be connected to the IR LED constant current source 20 in a parallel network with individual electrical switches for each LED 9 being implemented.

The USB-hub 19 is connected via a USB 2.0 cable 25 to a pre-processing unit 26. The signals pre-processed in the pre-processing unit 26 are finally analyzed in a personal computer 27, which contains a recorder device 28. An additional aux-/sync-port 13 forming an interface on the spectacle device 1 can also be connected to the USB-hub 19. The aux-/sync-port 13 can serve as interface for synchronization with other electronic devices or for triggering parallel data acquisitions. The electronics 15, pre-processing unit 16, USB-hub 19 and IR LED constant current source 20 are located on a common printed circuit board PCB 23.

In analogy to this setup the scene camera 2 is also connected to electronics 15 via a 100 mm cable 14. In this case the electronics 15 are located on a second printed circuit board PCB 24, which also contains a pre-processing unit 17. The pre-processing unit 17 can be based on electronics according to the DaVinci digital signal processor (DSP). It contains an MPEG encoder 18 for encoding the signals received from the electronics 15. A microphone 12 may also be connected to the pre-processing unit 17. The pre-processing unit 17 located on the PCB 24 is connected to the USB-hub 19. This way, processing signals acquired by the scene camera 2 are finally analyzed in the personal computer 27.

The pre-processing units 6, 16, 17 and 26 may be able to compress at least one of the three image streams generated by the two eye cameras 3l and 3r and the scene camera 2. Here, different alternatives are possible. A pre-processing unit may compress only the image stream of one camera while each camera has its own pre-processing unit. Alternatively, a single pre-processing unit may compress the image streams of all cameras. Furthermore, the pre-processing units may be configurable via a system interface and corresponding software to manage the bandwidth by adjustment of resolution, region of interest, frame rate and compression parameters. The pre-processing units may be designed to trigger synchronously the camera's image acquisition. They may provide time stamps for each acquired image which can be used to synchronise several or all camera data streams offline.

The pre-processing units may either be located on integrated circuit boards of the cameras or on a separate integrated circuit board that is located at or on a head mount (e. g. in the side bar 5l or 5r of the spectacle device 1) or in a separate housing that is worn by the test person 31, e.g. on a belt.

The spectacle device 1 may also comprise an auxiliary interface which allows to acquire data in real time from external sensors. Such sensors may be biometric sensors (including but not limited to EEG, ECG, etc.) or attitude sensors (including but not limited to accelerometers, magnetometers, gyroscopes, etc.). It is then possible to synchronise the data stream of the external sensors with the data streams acquired from the cameras 2, 3l and 3r. Furthermore, an external clock or trigger signal can be provided that can be used by the external sensors to synchronise themselves with the system. The bandwidth of data acquired from the interface can be reduced or compressed by means of on-board processing resources integrated in the system in its dedicated recording unit 28.

The eye cameras 3l and 3r can either be suited for visible or near infrared light. They are located symmetrically with respect to a vertical centre line that divides the user's face into two halves. The eye cameras 3l and 3r may be positioned in front and below the eyes 10l and 10r respectively, for example in or at the lower rim of a pair of eye glass lenses 8l and 8r, pointing at the eyes 10l and 10r in an angle of 30° to 50° and being mounted in the frame 4 in an angle a of 30° to 50°.

In the embodiment the eye cameras 3l and 3r are sensitive in the near infrared. They have a resolution of 640*480 and are read out with a 60 Hz frequency.

The scene camera 2 can be located on a vertical centre line that divides the user's face into two halves in or at the nose bridge of the frame 4. Alternatively, it may also be located at, in or close to the rim of a helmet, cap or headband. The scene camera 2 may have HD (high definition) and/or adjustable resolution of at least 720p (1280×720 pixels) and is operated at 30 Hz or 60 Hz. It can either be mounted in landscape or portrait orientation. Furthermore, it can be mounted such that its orientation can be changed from landscape to portrait orientation (camera roll) and also the direction the camera is pointing in (camera pan and tilt).

Instead of a single scene camera 2, the spectacle device 1 can also comprise a pair of scene cameras, where each scene camera can be oriented either in portrait mode or in landscape mode. Furthermore, each scene camera can be oriented independently of the respective second scene camera. Alternatively, both scene cameras 2 may have fixed orientations, which may or may not differ from each other.

Furthermore a prism or lens can be mounted in front of the scene camera 2 to create a different positioning of the field of view of the scene camera 2 with respect to the glasses, especially a more downward oriented field of view for near range reading applications.

Six LEDs 9 are located around each eyeglass lens 8. They emit in the infrared wavelength range (typically above 750 nm and below 1000 nm) at a central wavelength of 850 nm. They are driven by 50 mA current provided by the IR LED constant current source 20.

Instead of direct illumination of the eyes with the LEDs 9 also an implementation with a light guide can be envisaged. One or several segments of light guides (e.g. fiber optics) may be used. The illumination of the eyes may be implemented with focusing optics (structured illumination). Instead of the LEDs 9 suitable diffractive optics or lasers may be used to generate a pattern of coherent light for illuminating the eyes. The light source can be used together with an optical element in order to create a pattern of reflections on the eyes 10*l* and 10*r* (e.g. with focusing optics or diffractive optics). The illumination source may either emit visible or near infrared light. The illumination source may be positioned in or on the frame 4, in particular in a circle-like arrangement around the eye glass lenses 8*l* and 8*r*. Alternatively, the illumination source may be located on the rim or frame of a head mounted display. It may specifically be designed to create a pattern of reflections on the eye surfaces of the test person 31.

When the spectacle device 1 shown in FIG. 2 is worn by a test person the situation shown in FIG. 10A in a simplified way is realized. The eye camera 3 is arranged in such a way on the frame 4 that with the spectacle device 1 fixed to the head of a test person the optical path M capturing at least one parameter of the eye 10 extends in a straight line from the eye camera 3 to the eye 10.

FIGS. 3 and 10B show a different configuration of the spectacle device 1. The spectacle device 1 comprises a mirror 11, forming an optical deflection element attached to the frame 4, the mirror 11 and the eye camera 3 being arranged in such a way on the frame 4 that with the spectacle device 1 fixed to the head of the test person the optical path M for capturing at least one parameter of the eye 10 extends from the eye camera 3 via the mirror 11 to the eye 10. The three dimensional representation of FIG. 3 shows the spectacle device 1 from a rear or inside view. In the figure, reflections of the left and right eye 10*l* and 10*r*, respectively, show in the eyeglass lenses 8*l* and 8*r*. The coordinate system is a Cartesian one with the z-axis being directed into the plane of projection.

Thus, the eye cameras 3*l* and 3*r* may be mounted in front of and above the eyes 10*l* and 10*r* with an optical guide or mirror 11 located in front and below the eyes 10*l* and 10*r*, for example in or at the lower rim of a pair of eye glass lenses 8*l* and 8*r* in order to acquire an image of each eye 10*l* and 10*r* from a forward and low perspective and to make that image visible to the eye cameras 10*l* and 10*r*. The optical guide or mirror 11 can either be a (flat) mirror, a spherical mirror, a dome, a custom lens, a holographic image guide, etc. The mirror 11 can be reflecting only a specific range of wavelength and be transparent to others.

The mirror 11 can either be a flat mirror or a spherical mirror. The advantage of a spherical mirror is that it magnifies the field of view of the eye camera 3 beyond the field of view achievable with a flat mirror. The configuration of FIG. 3 furthermore allows to place the optical system very close to the eye 10 (set direction) thus improving ergonomics and aesthetics. The test person's own field of view is hardly obstructed. The mirror 11 can be a so-called hot mirror, i.e. the mirror 11 is transparent in the visible wavelength range while having a higher reflectivity in the infrared wavelength range. It can be very thin and hollow (so-called dome) thus, minimizing the distortion due to refraction. It can be made out of a material showing a very low index of refraction (10R).

In both cases (FIGS. 10A and 10B) the eye camera 3 is arranged in such a way that the optical path M for the capturing of at least one parameter of the eye 10 excludes the frame insert, i.e., the eye glass lens 8. Furthermore, the eye glass lens 8 is arranged in such a way that the optical axis K of the eye 10 and the optical path M as single jointly used optical element comprise the eye 10. Furthermore, the optical path M entirely runs within a space Sp which extends on the side of the eye glass lens 8 facing the eye 10.

The embodiments shown in FIGS. 2 and 3 and FIGS. 10A and 10B, respectively, both reduce eye occlusion due to the upper eye-lid.

FIGS. 6A to 8 illustrate the reduction of parallax errors in the spectacle device 1 compared to the prior art. As can be seen in FIG. 6A the position of an object 29 the test person actually focuses its eyes on and the point of regard 32 determined by the spectacle device 1 usually do not coincide very well when using spectacle devices 1 as known from the prior art. This effect is usually the more pronounced the closer the test person is located to the object 29 that is to be focused. However, with the spectacle device 1 according to an embodiment of the invention the coincidence between the determined point of regard 32 and the actual object 29 is very good, even for measuring distances as low as 0.5 m (see FIG. 6B). This is achieved by minimizing the distance between the eye ball center and the camera focal point.

The situation is again illustrated in FIG. 7. As eye 10 and scene camera 2 are located at slightly different positions the difference in their respective viewing angles for focussing the object 29 becomes the more pronounced the closer the object 29 is located to the eye 10 and scene camera 2, respectively (i.e. larger distortions for smaller z-values). The spectacle device 1 may get calibrated in the situation shown in FIG. 6B. The object 29 then lies in the calibration plain P and by calibrating the spectacle device 1 one can make sure that the determined point of regard 32 indeed falls onto the actual object 29. Calibration is typically performed on a plane at some distance from the test subject. It relates measured gaze direction (angles) to pixels in the scene video frame. This calculation gives valid results only for points that lie in that calibration plane. For points that do not lie on that plane, a systematic error (parallax) is introduced. When the distance of the spectacle device from the object 29 is increased the difference between the distance to the calibration plain P and the actual distance to the object 29 causes the pronounced deviations. With the spectacle device 1 according to an embodiment of the invention these deviations or parallax errors (indicated by symbols S2, circles, in FIG. 8) for all distances d are considerably smaller than with devices according to the prior art (symbols S1, rectangles). Thin-lined crosses relate to the group of symbols S2, while bold crosses relate to the group of symbols S1. The crosses correspond to the point of regard 32 used for calibration purposes.

The parallax error is mathematically modelled as a function of the position of the scene camera 2 with respect to the eye position. The gaze estimation error due to parallax is minimized by placing the scene camera 2 as close as possible to the eye 10, according to the results shown by the mathematical simulation. The parallax error can be further corrected by estimating the distance to the point of regard by using vergence from binocular tracking and by estimating the position of the eyes with respect to the eye tracking device.

To achieve even better results the field of view of the scene camera 2 can be optimized. The scene camera 2 with standard optics has a field of view that does not cover the full physiological gaze range (horizontal field of view of standard optics: 40° to 50°; typical physiological gaze range: 60°). In an embodiment the field of view of the scene camera 2 can thus be optimized depending on the respective application. One such field of view optimization method is illustrated in FIGS. 9A and 9B. A user wearing the spectacle device 1 is at the same time observing a background B and his mobile phone 30. According to FIG. 9A the field of view FOV1 mainly covers the background B. When the test person 31 looks down onto its mobile phone 30 the change in gaze direction is automatically determined by the eye cameras 3l and 3r and the scene camera's 2 field of view is automatically adjusted by switching from landscape to portrait orientation (field of view FOV2). This can be achieved by a z-axis 90° mechanical roll of the scene camera 2 or by the use of an optical prism in front of the scene camera 2. Also the use of two scene cameras with different tilt or roll angles is possible. Alternatively, also an optical beam splitter may be used in front of the scene camera 2.

In summary, the spectacle device 1 forms a head-mounted eye tracking system which consists of three cameras: two eye cameras 3l and 3r and at least one scene camera 2. The three cameras 3l, 3r and 2 can have a manageable bandwidth, for example by adjustable frame rates or resolutions. One or several pre-processing units 6, 16, 17 and 26 may exist that perform variable compression of the video streams received from the cameras 2, 3l and 3r. The level of compression of the video streams may be the same for the eye cameras 3l and 3r and the scene camera 2, or the video streams may be separately compressed for the eye cameras 3l and 3r and the scene camera 2. The frame rate for eye camera 31 may correspond to full speed acquisition, the one of eye camera 3r may correspond to 1/10 speed acquisition and the one for the scene camera 2 may correspond to 1/2 speed acquisition. Instead of adjusting the frame rates of the different cameras, alternatively the acquisition rates may be chosen to be the same, while data processing is performed differently for each camera. Data provided by one camera may be compressed more than data provided by another camera, although both cameras acquire the same amount of data. One may also combine different compression rates with different acquisition rates. It is also possible to omit, for example, every second acquired image when transferring the data and thus reduce the amount of data to be sent to the CPU by half. The signals of the cameras 2, 3l and 3r may be transferred to a CPU in the PC 27 via a wired or wireless interface (see FIG. 5). Auxiliary interfaces for other data sources and methods for synchronisation with these data sources may be implemented in the spectacle device 1.

The spectacle device 1 can come as a system comprising several exchangeable pieces. The spectacle device 1 can have an exchangeable set of nose pieces or nose supports 7 for faces with small or large noses. This way, the spectacle device 1 can be worn over vision correction glasses without a problem. Furthermore, the spectacle device 1 has a holding mechanism for exchangeable glasses that can have different levels of light transmittance (e.g. clear glasses or sun glasses) for a certain range of wavelengths. Additionally or alternatively the exchangeable glasses can have a near infrared optical filter to match the wavelength of the illumination source and block some or all light from the outside of same and similar wavelengths from reaching the eye surface to improve signal to noise on the eye surface. The spectacle device 1 has rims and a nose bridge that serve as a mount or housing for the eye cameras 3l and 3r and the scene camera 2. The eye cameras 3l and 3r are mounted in such a way that their field of view extends behind the exchangeable glasses 8l and 8r.

With the spectacle device 1 it is possible to do eye tracking, occulometrics, biometrics and position and motion measurements in order to measure and classify as fully as possible human behaviour in a free range movement setup. A head mounted eye tracking device is realised which is calibration-free and provides an astigmatism estimation. The eye-tracking functionality has zero set-up time. No adjustments are necessary. A test person 31 can just put the spectacle device 1 on and start using it. It has a very large gaze-tracking range covering the physiological range of human eye movement (80° horizontal, 60° vertical). It is very robust and has a high accuracy in gaze mapping. Astigmatism is compensated for, parallax is minimized, pupil axis shift is compensated and the device is calibration free or can be calibrated using a one-point calibration feature. Furthermore, it is designed to work irrespective of ethnic group (Caucasian, Asian, African, etc.), gender and age. The field of view of the scene camera 2 is optimized. By the use of optical, inertial or magnetic sensors a head tracking functionality can be implemented. The spectacle device furthermore offers biometric features, such as measuring the pupil diameter and offering interfacing and synchronisation options with EEG, ECG, etc. Finally, it can be integrated with a head mounted display. It is possible to project a virtual image onto a subject's eye of a portable computer screen. Furthermore, the possibility is offered to interact with "objects" in the virtual image using eye movement (gaze, blinks).

Head tracking functionality can be realized by the use of three axis gyroscopes, three axis accelerometers and/or three axis magnetometers with optional sensor fusion for six dimensional head tracking.

In summary, the spectacle device 1 offers a very specific optical and electronic architecture. With respect to the electronic architecture three or more high resolution cameras with allocateable bandwidth are incorporated in the device 1. Separate processing channels for eye cameras 3l and 3r and the scene camera 2 are envisaged. The optical architecture is characterized by exchangeable glasses with various properties. The optical path of the eye cameras 3l and 3r extends behind the glasses or eye glass lenses 8l and 8r respectively. Furthermore, a set of LEDs 9 allows for highly variable illumination of the eyes 10l and 10r. For instance, the illumination geometry around the eye can be controlled. The specific LED subsets can be controlled with regard to strobe effect and sequencing. Finally, eye illumination can be achieved by point, line or two-dimensional light sources.

REFERENCE SIGNS 1 spectacle device
2 scene camera
3, 3l, 3r eye camera 4 frame
5l, 5r side bar
6 pre-processing unit
7 nose support
8, 8l, 8r eyeglass lens
9 LED
10, 10l, 10r eye
11 mirror
12 microphone
13 aux-/sync-port
14 cable
15 electronics
16 pre-processing unit
17 pre-processing unit
18 MPEG encoder
19 USB hub
20 IR LED constant current source
21, 22 IR LED chain
23, 24 PCB
25 USB 2.0 cable
26 pre-processing unit
27 PC
28 recorder
29 object
30 mobile phone
31 test person
32 point of regard
w1, w2 width
h height
l length
a tilt angle
K optical axis
M optical path
O origin of system of reference
P calibration plane
Sp space
d distance
S1, S2 symbols
B background
FOV1, FOV2 field of view
x, y, z axis

The invention claimed is:

1. An optical measuring device for capturing at least one parameter of at least one eye of a test person wearing the optical measuring device, comprising:
a frame, which is configured to fix the optical measuring device to the head of the test person,
at least one capturing unit, which is configured to optically capture the at least one parameter of the at least one eye, and
an illumination unit for illuminating the at least one eye, and adjusting an illumination characteristic in correlation with the capturing performed by the capturing unit,
wherein the at least one capturing unit is configured to capture and discern the illumination characteristic, and
wherein the illumination unit is configured to be adjustable with regard to a spatial structured illumination distribution to provide the adjusted illumination characteristic.

2. The optical measuring device according to claim 1, wherein:
the illumination unit is attached to the frame in such a way that with the optical measuring device fixed to the head of the test person it faces the at least one eye and is configured to emit radiation in such a way that the radiation at least partly hits the at least one eye.

3. The optical measuring device according to claim 1, wherein:
the illumination unit comprises at least two illumination segments which with regard to their luminosity, or luminous color, or main radiation direction, or temporal sequence of the light emission, or any combination thereof, are separately adjustable.

4. The optical measuring device according to claim 1, wherein:
the illumination unit comprises at least one optical waveguide and/or at least two illuminants, in particular light-emitting diodes.

5. The optical measuring device according to claim 1, wherein:
the illumination unit is configured to emit visible light and/or light in the infrared spectral range.

6. The optical measuring device according to claim 1, wherein:
the frame comprises at least one frame element for receiving an eyeglass lens, wherein with the optical measuring device fixed to the head of the test person the portion framed by the frame element is positioned in front of the at least one eye of the test person, and the illumination unit is arranged on or within the frame element.

7. The optical measuring device according to claim 1, wherein:
the at least one capturable parameter concerns an orientation, or a position, or an eyelid closure, or a pupil diameter, or a limbus characteristic, or a sclera characteristic, or an iris characteristic, or a characteristic of a blood vessel, or a cornea characteristic of the at least one eye, or any combination thereof.

8. A method for capturing at least one parameter of at least one eye of a test person, by means of a measuring device fixed to the head of the test person, the method comprising:
illuminating the at least one eye; and
optically capturing the at least one parameter of the at least one eye,
setting an illumination characteristic; and
illuminating the at least one eye according to the set illumination characteristic;
wherein the illuminating is regulated in dependency of a spatial, structured illumination distribution to provide the illumination characteristic and the illumination characteristic is correlated to the capturing, wherein the capturing captures and discerns the illumination characteristic.

9. The method according to claim 8, wherein:
optically capturing the at least one parameter of the at least one eye comprises:
optically capturing of at least two light reflections and/or features of the at least one eye; and
determining the at least one parameter of the at least one eye by means of the captured light reflections and/or features.

10. The method according to claim 9, wherein:
the at least two light reflections and/or features are captured at different illuminations.

11. The method according to claim 8, wherein:
capturing data which concern a viewing behavior of the test person, or an eye motion characteristic, or a pupil change, or an environmental condition, or inputs of the test person, or any combination of the thereof;
in dependency on the captured data, setting an illumination program for the spatial illumination distribution;
regulating the spatial illumination distribution according to the set illumination program.

12. An optical measuring device for capturing at least one parameter of at least one eye of a test person wearing the optical measuring device, comprising:
- a frame, which is configured to fix the optical measuring device to the head of the test person,
- at least one capturing unit, which is configured to optically capture the at least one parameter of the at least one eye, and
- an illumination unit for illuminating the at least one eye and adjusting an illumination characteristic;
- wherein the illumination unit comprises at least two illumination segments, which are separately adjustable with regard to at least one of their illumination characteristics.

13. A method for capturing at least one parameter of at least one eye of a test person, by means of a measuring device fixed to the head of the test person, the method comprising:
- illuminating the at least one eye; and
- optically capturing the at least one parameter of the at least one eye,
- setting an illumination characteristic; and
- illuminating the at least one eye according to the set illumination characteristic, wherein the illuminating comprises at least two illumination segments which are adjusted separately with regard to at least one of their illumination characteristics.

14. An optical measuring device for capturing at least one parameter of at least one eye of a test person wearing the optical measuring device, comprising:
- a frame, which is configured to fix the optical measuring device to the head of the test person,
- at least one capturing unit, which is configured to optically capture the at least one parameter of the at least one eye, and
- an illumination unit for illuminating the at least one eye and adjusting an illumination characteristic,
- wherein the optical measuring device is configured to:
  - capture data which concern a viewing behavior of the test person or an eye motion characteristic or a pupil change or an environmental condition or inputs of the test person;
  - in dependency on the captured data, set an illumination program for the temporal or spatial illumination distribution or the illumination pattern; and
  - regulate the temporal illumination sequence or the spatial illumination distribution or the illumination pattern according to said illumination program.

15. A method for capturing at least one parameter of at least one eye of a test person, by means of a measuring device fixed to the head of the test person, the method comprising:
- illuminating the at least one eye;
- optically capturing the at least one parameter of the at least one eye,
- setting an illumination characteristic;
- illuminating the at least one eye according to the set illumination characteristic,
- capturing data which concern a viewing behavior of the test person or an eye motion characteristic or a pupil change or an environmental condition or inputs of the test person; and
- in dependency on the captured data, setting an illumination program for the temporal, or spatial, or both temporal and spatial, illumination distribution, or for the illumination pattern or for both; and
- regulating (1) at least one of the temporal illumination sequence and the spatial illumination distribution, or (2) the illumination pattern, or (3) both (1) and (2), according to said illumination program.

16. The optical measuring device according to claim 1, wherein:
- the capturing unit is configured to discriminate between deliberate reflections and reflections resulting from undesired stray light on the basis of the illumination characteristic.

17. The method according to claim 8, further comprising:
- discriminating between deliberate reflections and reflections resulting from undesired stray light on the basis of the illumination characteristic.

18. The optical measuring device according to claim 12, wherein:
- the at least two illumination segments are separately adjustable with regard to at least one characteristic of luminosity, wavelength, main radiation direction and temporal sequence of the light emission to provide the illumination characteristic, and
- the capturing unit is configured to capture and discern the illumination characteristic to discriminate between deliberate reflections and reflections resulting from undesired stray light on the basis of the illumination characteristic.

19. The method according to claim 13, wherein:
- the at least two illumination segments are adjusted separately with regard to at least one characteristic of luminosity, wavelength, main radiation direction and temporal sequence of the light emission to provide the illumination characteristic, and
- the capturing captures and discerns the illumination characteristic to discriminate between deliberate reflections and reflections resulting from undesired stray light on the basis of the illumination characteristic.

20. The optical measuring device according to claim 12, wherein:
- the at least two illumination segments are separate, individual and, with regard to their illumination characteristics, homogenous entities within the illumination unit, and
- the at least two illumination segments are spatially separated.

21. The optical measuring device according to claim 20, wherein:
- the frame contains at least one opening, which is filled with a frame insert,
- the frame comprises a rim that encloses the frame insert, and
- the at least two illumination segments are spatially separated located along the rim.

22. An optical measuring device for capturing at least one parameter of at least one eye of a test person wearing the optical measuring device, comprising:
- a frame, which is configured to fix the optical measuring device to the head of the test person,
- at least one capturing unit, which is configured to optically capture the at least one parameter of the at least one eye, and
- an illumination unit for illuminating the at least one eye and adjusting an illumination characteristic,
- wherein the frame contains at least one opening, which is filled with a lens,
- wherein the frame comprises a rim that encloses the lens,
- wherein the capturing unit comprises at least one eye camera integrated into the rim in front of the at least one eye, and wherein the eye camera is arranged such that the optical path for the capturing of the at least one parameter of the eye excludes the lens.

\* \* \* \* \*